(12) United States Patent
Lin

(10) Patent No.: US 7,185,527 B2
(45) Date of Patent: Mar. 6, 2007

(54) PROTECTING FILAMENTS OF A THERMAL CONDUCTIVITY DETECTOR

(75) Inventor: Bing-yi Lin, Shanghai (CN)

(73) Assignee: Agilent Technologies, Inc., Santa Clara, CA (US)

( * ) Notice: Subject to any disclaimer, the term of this patent is extended or adjusted under 35 U.S.C. 154(b) by 0 days.

(21) Appl. No.: 11/232,179

(22) Filed: Sep. 20, 2005

(65) Prior Publication Data
US 2006/0236751 A1 Oct. 26, 2006

(30) Foreign Application Priority Data
Apr. 21, 2005 (CN) .................. 2005 1 0066198

(51) Int. Cl.
G01N 30/02 (2006.01)
(52) U.S. Cl. .................... 73/23.4; 73/25.03
(58) Field of Classification Search ............. 73/23.4, 73/25.03, 19.02, 19.01, 23.2, 23.35, 23.42
See application file for complete search history.

(56) References Cited

U.S. PATENT DOCUMENTS

| | | | | |
|---|---|---|---|---|
| 4,254,654 A | * | 3/1981 | Clouser et al. | 73/23.4 |
| 4,316,381 A | * | 2/1982 | Woodruff | 73/31.05 |
| 4,316,382 A | * | 2/1982 | Woodruff | 73/23.2 |
| 4,670,220 A | * | 6/1987 | Wells | 422/103 |
| 6,928,858 B2 | * | 8/2005 | Lin | 73/25.03 |

* cited by examiner

Primary Examiner—Hezron Williams
Assistant Examiner—Ryan Christensen

(57) ABSTRACT

A process for protecting a filament in a thermal conductivity detector from chemical corrosion includes changing the flow direction of the column effluent in the thermal conductivity detector to allow the column effluent to bypass the filament when an undesired compound appears in the column effluent. The flow direction of the column effluent in the thermal conductivity detector is changed when the undesired compound disappears from the column effluent to allow the column effluent to pass through the filament. A thermal conductivity detector that allows the column effluent to (1) bypass the filament when an undesired compound appears in the column effluent and (2) pass through the filament when the undesired compound disappears in the column effluent is also described.

8 Claims, 4 Drawing Sheets

PROTECTING FILAMENTS OF A THERMAL CONDUCTIVITY DETECTOR

TECHNICAL FIELD

The various embodiments of the present invention relate generally to a thermal conductivity detector (TCD) for a gas chromatograph, and in particular, to protecting filaments in a TCD from chemical corrosion.

BACKGROUND

Gas chromatographs are widely used to measure quantities of various chemicals in a mixture. A very small amount of liquid mixture (i.e., sample) is injected into the instrument and is vaporized in a hot chamber. The sample gas is then pushed by a stream of inert carrier gas through a chromatographic column. This causes various chemicals in the sample gas to take different amounts of time to pass through the column and so appear as sequential concentrations in the stream of carrier gas flowing out of the column. A detector is coupled to the output of the column to detect the existence of these chemicals in the column effluent and their amounts. The term "column effluent" as used herein means a portion of the sample gas that is being eluted out of a chromatographic column at a given time plus a portion of the carrier gas.

One such detector is commonly referred to as a thermal conductivity detector (TCD). Two types of TCDs are known by those skilled in the art. One is a dual-filament TCD. The other type of TCD is a single-filament TCD. FIG. 1 shows an example of one prior art single-filament TCD 10 that has two cavities 12 and 14 and one filament 18 suspended in the cavity 12. The filament 18 is heated to a preset constant temperature. A switch valve 16 is employed to switch at a predetermined frequency, e.g. 5 Hz, throughout the whole detection process, so that the inert carrier gas from a source 100 and the effluent from a column 19 alternatively flow through the filament 18. This causes the voltage required to keep the filament 18 at a given temperature to vary. The voltage is measured and processed, giving rise to an electrical signal which indicates the different compositions in the sample gas.

However, this prior art detector suffers from a gradual decrease in sensitivity due to chemical corrosion of the filament caused by the sample gas. Although the filament is usually fabricated from corrosion-resistant materials, such as Rhenium (Re), Tungsten (W) or Re—W alloy, and has been chemically passivated to protect against oxygen damage, chemical compounds such as acids and halogenated compounds may still attack the filament causing its sensitivity to decrease dramatically. Thus, after some period of time in operation, the filament has to be replaced, resulting in economic loss and inconvenience of operation.

In view of the above problems, it is desirable to protect the TCD filament from chemical corrosion and to prolong its lifespan.

SUMMARY

In accordance with one embodiment of the present invention, a process for protecting a filament in a thermal conductivity detector includes changing the flow direction of column effluent in the thermal conductivity detector to allow the column effluent to bypass the filament when an undesired compound appears in the column effluent. The flow direction of the column effluent in the thermal conductivity detector is changed to allow the column effluent to pass through the filament when the undesired compound disappears from the column effluent.

In accordance with another embodiment the present invention, a thermal conductivity detector for a gas chromatograph includes a first and a second cavity, each having a separate inlet. The cavities share a common inlet. The common inlet is coupled with the outlet of a chromatographic column. A switch valve is coupled to a carrier gas supply source and the separate inlets of the first and second cavities. A filament is positioned in the first cavity. A controller is coupled to the switch valve to control the switch valve to change the flow direction of the column effluent in the thermal conductivity detector (1) to allow the column effluent to bypass the filament when an undesired compound appears in the column effluent and (2) to allow the column effluent to pass through the filament when the undesired compound disappears in the column effluent.

BRIEF DESCRIPTION OF THE DRAWINGS

The accompanying drawings, which are incorporated in and form a part of this specification, illustrate various embodiments of the present invention. Like reference numbers generally indicate identical, functionally similar, and/or structurally equivalent elements. It should be understood that the drawings are not drawn to scale. In the drawings.

DETAILED DESCRIPTION

In the following detailed description, numerous specific details are set forth in order to provide a thorough understanding of the various embodiments of the present invention. However, it will be recognized that embodiments of the present invention may be practiced without these specific details. In addition, certain well-known methods, procedures, components and circuit have not been described in detail so as not to unnecessarily obscure aspects of the present invention.

Figure 2A:
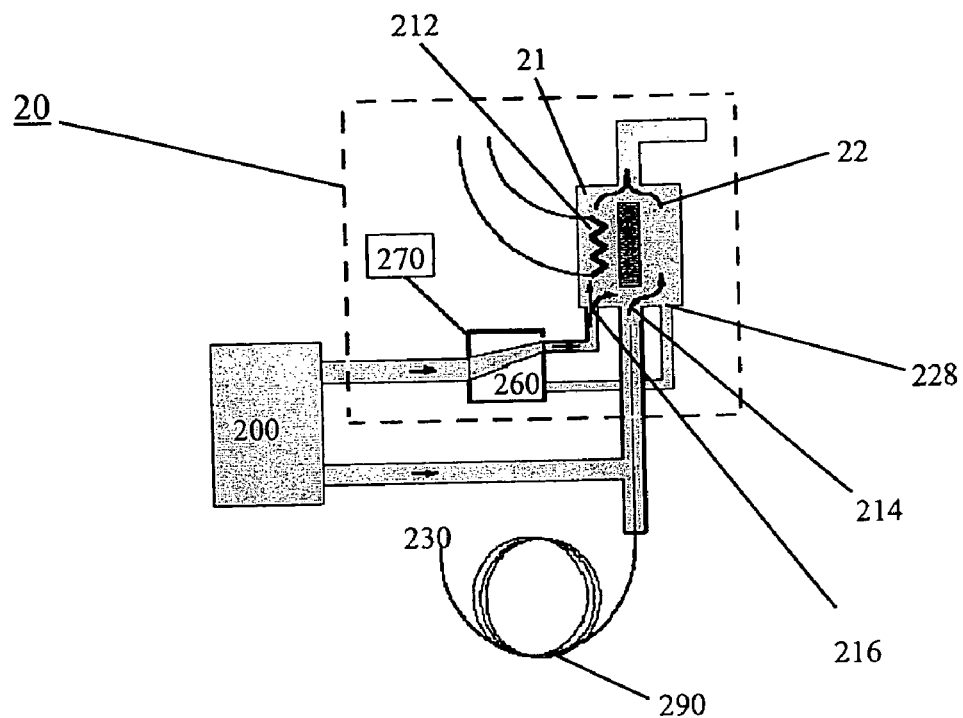
FIGS. 2A and 2B illustrate a single-filament TCD that implements one embodiment of the present invention.
Figure 2B:
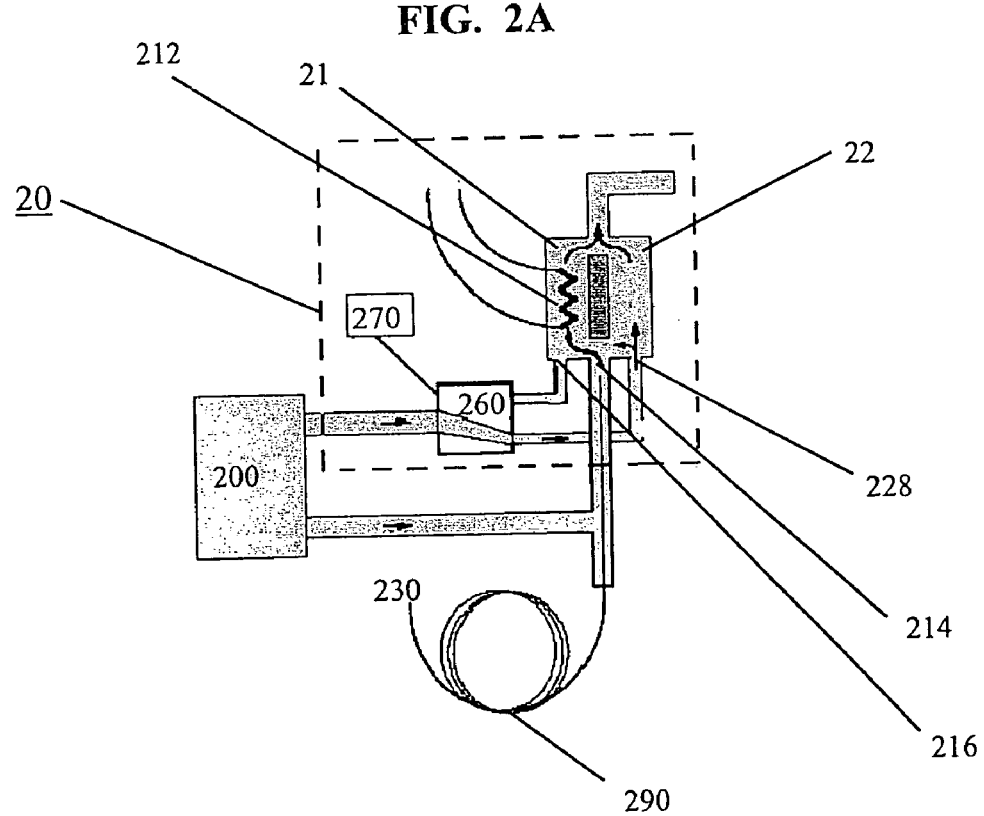

FIGS. 2A and 2B show a single-filament thermal conductivity detector (hereinafter "TCD") 20 in accordance with one embodiment of the present invention. The TCD 20, which is denoted by the dashed-line square, includes two cavities 21 and 22, but only the cavity 21 contains a filament 212, which forms a Wheatstone Bridge circuit together with other circuit elements (not shown). The cavities 21 and 22 have separate inlets 216 and is 228, respectively, and share a common inlet 214. The TCD 20 further includes a switch valve 260 and a controller 270 coupled to the valve 260. The switch valve 260 is positioned between a carrier gas source 200 and the inlets 216 and 228, such that the inlet of the valve 260 is connected to the carrier gas source 200 while the two outlets of the valve 260 are connected to the inlets 216 and 228, respectively. With such an arrangement, the switch valve 260 can divert the flow of carrier gas toward the inlet 216 or 228 under the control of the controller 270.

In one embodiment, the valve 260 is an electromagnetic switch valve capable of switching the flow direction of a fluid flowing therethrough at a predetermined frequency, e.g. 5 Hz. The valve 260 can be, example, the LHD Series Valves manufactured by The Lee Company can be used as the switch valve 260. The valve 260 will not be described in more detail below. Other types of switch valves can also be used provided that they can switch the flow direction of a fluid automatically under the control of the controller 270.

The inlet 214 is also connected to a chromatographic column 290 of a gas chromatograph (not shown). When an analytical test is performed by the gas chromatograph on a sample, the sample is injected from the sample inlet 230, flows through the chromatographic column 290 and then enters into the TCD 20 through the common inlet 214, together with a portion of carrier gas (referred to as makeup gas), if necessary. At the same time, a portion of carrier gas (referred to as reference gas) flows through the switch valve 260 and then enters into the TCD 20 through the separate inlet 216 or 228. In one embodiment, the carrier gas is Helium.

Two operation modes are available for the TCD 20, including a "normal" mode and a "bypass" mode. In the normal mode, the switch valve 260 alternates between the positions of inlets 216 and 228 at a predetermined frequency, e.g. 5 Hz. When the valve 260 is switched to the inlet 216, as illustrated in FIG. 2A, only the reference gas flows through the filament 212 while the column effluent and a portion of the reference gas passes through the cavity 22. The term "column effluent" as used herein means a portion of the sample gas that is being eluted out of the column 290 at a given time plus a portion of the makeup gas.

However, when the valve 260 is switched to the inlet 228 in the "normal" mode, as illustrated in FIG. 2B, the column effluent and a portion of the reference gas flow through the filament 212 while the other portion of the reference gas passes through the cavity 22. The periodic alternating causes a variation in the thermal conductivity of the filament 212 and the changes of the electrical signals derived from the bridge circuit. Following this, a chromatogram can be obtained after mathematical processing of the resulting electrical signals.

In the "bypass" mode, the controller 270 issues a command to set the valve 260 toward a position corresponding to the inlet 216 of the cavity 21 and to keep it unchanged for a period of time, i.e. to keep the valve 260 in the status as illustrated in FIG. 2A. Thus, only the reference gas flows through the filament 212 while the column effluent is forced to bypasses the filament 212. As only the reference gas flows through the filament 212, a line substantially the same as the base line will appear in the resulting chromatogram.

The TCD 20 alternates between the normal mode and the bypass mode according to the controlling instructions of the controller 270. Generally, the default setting of the TCD 20 after startup is the normal mode; then it is changed into the bypass mode upon the occurrence of an undesired compound, e.g. a solvent or a corrosive compound harmful to the filament 212, in the column effluent; and then it is converted back to the normal mode after the undesired compound has disappeared. In this way, once the undesired compound in the sample gas is eluted from the chromatographic column 290, the column effluent will bypass the filament 212 to avoid corrosion of the filament 212. Then, once the undesired compound has been vented out, the TCD 20 is reverted back to the normal mode such that the analytical test continues without being adversely affected.

The occurrence time of the undesired compound can be determined by pretesting or according to the experience of the laboratory technician. Generally, the laboratory technician will perform several pre-tests to determine the operational parameters of the gas chromatograph before the formal experiment is carried out. Once the operational parameters have been determined in the pre-tests, the occurrence time of certain compound in the column effluent can be approximately estimated. For example, many kinds of samples require halogenated hydrocarbons as solvents, which are corrosive to the filament. Upon the completion of the pre-experimentation during which the operational parameters are optimized and determined, the occurrence time of the solvent-peak in the chromatogram will have been substantially determined. With such information it is possible to control the switch valve 260 by the controller 270 to avoid filament damage from the undesired compound, e.g. halogenated hydrocarbons.

The controller 270 can be constructed in various forms, depending on the demands of the specific applications. For example, the controller 270 may be a separate circuit or integrated circuit, in hardware or firmware form, or a processor. Alternatively, the controller 270 may be preferably integrated into the controller or CPU of the gas chromatograph or thermal conductivity detector because it requires only minor modification of the mechanical components in the prior TCD. In other words, the controller 270 can be preferably implemented by reprogramming a prior controller or CPU.

According to one embodiment of the present invention, the controller 270 includes a memory storing a Time Event Table for convenience of control. The laboratory technician can record the estimated occurrence time period(s) of the undesired compound(s) in the Time Event Table before experiment. Then, the controller 270 can issue an instruction to switch the switch valve 260 at the time specified by the Time Event Table. For example, in the case wherein halogenated hydrocarbons are used as solvent, the occurrence time period of the solvent-peak can be recorded in the Time Event Table. During the analytical experiment, the controller 270 will issue an instruction to set the TCD 20 to the bypass mode such that the solvent will bypass the filament 212 during the specified time period.

The logical structure of the Time Event Table depends on the specific demands of various applications. For example, Table 1 below is an illustrative logical structure for the Time Event Table. Table 1 comprises in total two rows of data. The first row of data indicates that the undesired compound will elute from the column within a time period of 20–50 s after the injection of the sample. During the experiment, the controller 270 reads the Time Event Table, issues a command to switch the valve 260 to the bypass mode at the 20 s mark and keep the bypass mode until the 50 s mark, and then issues a command to switch the valve 260 back to the normal mode at the 50 s mark. Thus, the undesired compound will bypass the filament 212 during the time period of 20–50 s, following which the experiment will then continue as normal. The second row uses two "0" as the terminator, indicating that only one time period of bypass mode is needed in this example. If the TCD 20 is required to work in the bypass mode over several time periods, additional rows of data can be inserted into the Time Event Table, as illustrated in Table 2.

TABLE 1

| No. | t1(s) | t2(s) |
|---|---|---|
| 1 | 20 | 50 |
| 2 | 0 | 0 |

TABLE 2

| No. | t1(s) | t2(s) |
|---|---|---|
| 1 | 20 | 50 |
| 2 | 80 | 100 |
| 3 | 180 | 240 |
| 4 | 0 | 0 |

The specific form of the Time Event Table will depend on the type of the controller and the programming language used. For example, it can be implemented by hardware, such as an Application Specific Integrated Circuit (ASIC). However, it is preferably implemented by reprogramming the prior controller of the gas chromatograph or thermal conductivity detector. Those skilled in the art, with a basic knowledge of software and hardware, can easily implement the above-described tables.

Further, it is to be understood that the above tables are for illustrative purpose only. A more complex Time Event Table may be used. Alternatively, the Time Event Table may be replaced by other controlling means, e.g. a real-time controller, which controls the switch valve based on the real-time detection of the undesired compounds. It is also possible to control the switch valve manually.

According to one embodiment of the present invention, the memory of the controller 270 may further store a flag indicative of the status of the valve 260 in order to facilitate the control of the valve 260 and to access the status of the valve 260. The flag is directly connected to the valve 260 and corresponds to its status. With respect to TCD 20, as the valve 260 can be worked in three different states the flag "SWITCH" has therefore three different values. In particular, SWITCH="AUTO" (or "0") represents the auto-alternating states at a predetermined frequency; SWITCH="ON" (or "1") indicates the bypass mode under which the valve 260 is set toward the inlet 216, as illustrated in FIG. 2A; and SWITCH="OFF" (or "2") indicates the valve 260 is set toward the inlet 228, as illustrated in FIG. 2B. (The last status is desirable under some special circumstances, but is not mentioned in embodiments of the present invention.) Hereby, the valve 260 can be easily controlled by setting the flag SWITCH in the memory, at the same time the status of the valve 260 can also be easily accessed by reading the flag SWITCH.

The term "memory" as used herein is intended to include various kinds of storage devices, such as, for example, RAM, ROM, a fixed memory device (e.g., hard drive), a removable memory device (e.g., diskette), flash memory, etc. The memory may be separated from the controller 270, or may be integrated into the controller 270.

The process for protecting a filament in a TCD can be performed using the TCD 20 illustrated in FIGS. 2A and 2B. For example, FIG. 3 illustrates a flow chart detailing the process for protecting a filament in a TCD according to one embodiment of the present invention.

Figure 3:
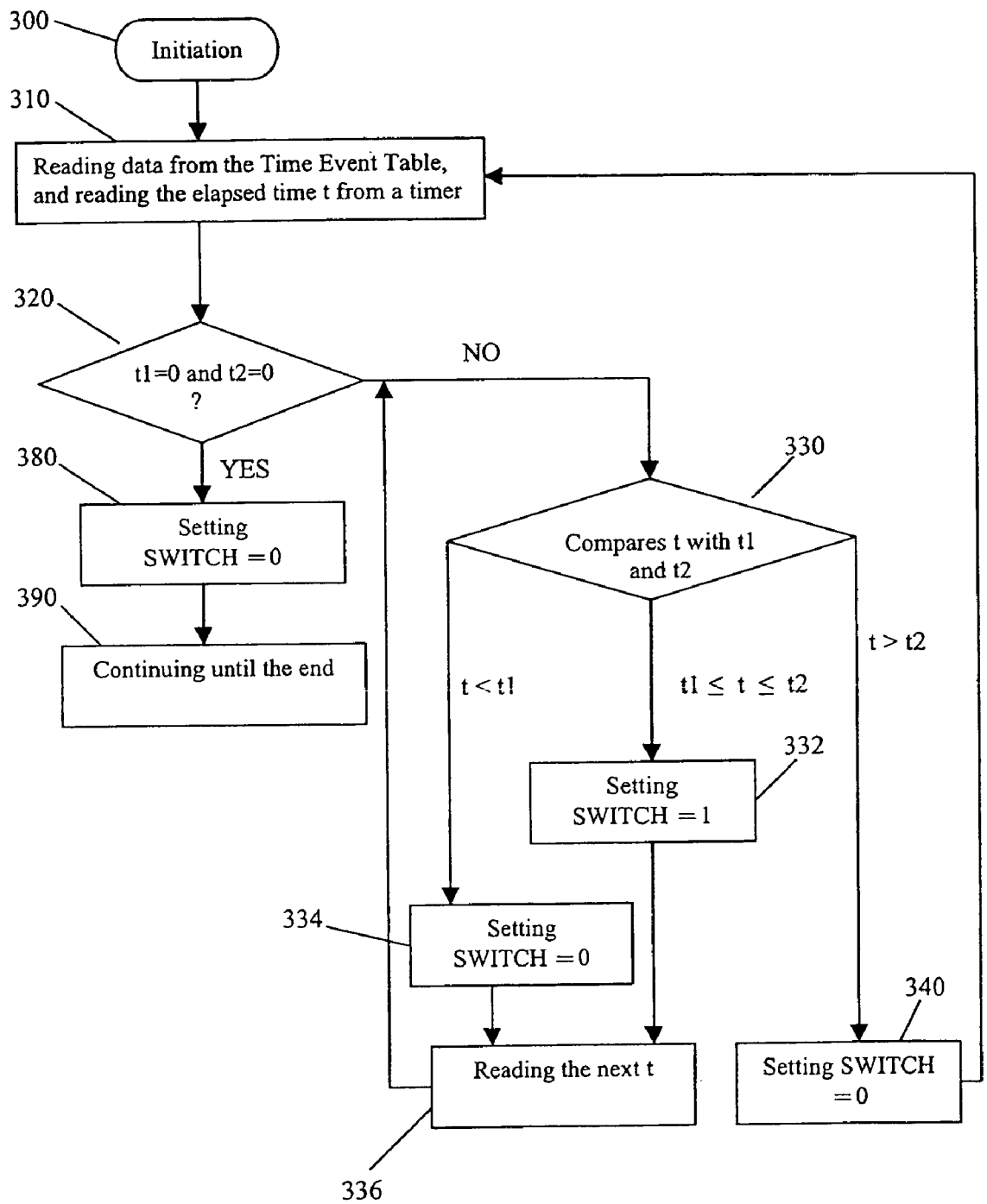
FIG. 3 is a flow chart illustrating a method for operating the TCD of FIGS. 2A and 2B according to one embodiment of the present invention.

Referring now to FIG. 3, the process begins with an initiation step (step 300), e.g. the resetting of a timer and/or setting of the default operation mode. Then, in Step 310, the controller 270 reads a row of data recorded in the Time Event Table, i.e. t1 and t2, and reads the elapsed time t through the timer. (The elapsed time t represents the time elapsed after injection of the sample.) In Step 320, it is determined whether the condition expression "t1=0 and t2=0" is satisfied. If yes, it indicates that no undesired compound is present in the sample or all the undesired compounds have already been eluted out of the column; the process proceeds to Step 380 during which the flag "SWITCH" is set to "0" to perform the normal detection, then the process continues until the end (Step 390). If the condition expression is not satisfied, the controller 270 compares t with t1 and t2 (Step 330) and performs different operations based on the different comparison results, as elaborated below. If t<t1, it indicates that no undesired compound appears in the column effluent, the controller 270 will set the flag "SWITCH" to "0" to perform the normal detection (Step 334) and then read the next elapsed time t to perform the next comparison step (Steps 336 and 330). If $t1 \leq t \leq t2$, it indicates that a undesired compound is being eluted out of the column; the controller 270 will set the flag "SWITCH" to "1" to switch the TCD 20 to bypass mode in which the undesired compound is diverted into the cavity 22 to protect the filament 212 (Step 332), and then the controller 270 will read the next elapsed time t to perform the next comparison step (Steps 336 and 330). If t>t2, it indicates that this kind of undesired compound has been completely eluted out of the column; the controller 270 will set the flag "SWITCH" to "0" again to restore the TCD 20 to normal mode (Step 340), and then the controller 270 will read the next elapsed time t and the next row of data in the Time Event Table (Step 310).

The above process described with reference to FIG. 3 can effectively protect the filament 212 against damage from various kinds of undesired chemicals harmful to the filament 212 without interrupting the normal detection process. For this reason, the lifespan of the filament 212 will be increased and experimental costs will be reduced. At the same time, the above process requires only minor modification of the mechanical components in the prior TCD and is therefore cost-effective. Further, it is easy to hide any undesired peaks in a chromatogram with the above process because the process allows any undesired compounds in the sample to bypass the filament 212.

One aspect of the present invention relates to a new gas chromatograph, which comprises the TCD according to an embodiment of the present invention. For example, the gas chromatographs 6890GC, 6820GC and 6850GC, manufactured by Agilent Technologies Inc. can be equipped with the TCD 20 to form new gas chromatographs.

Figure 1:
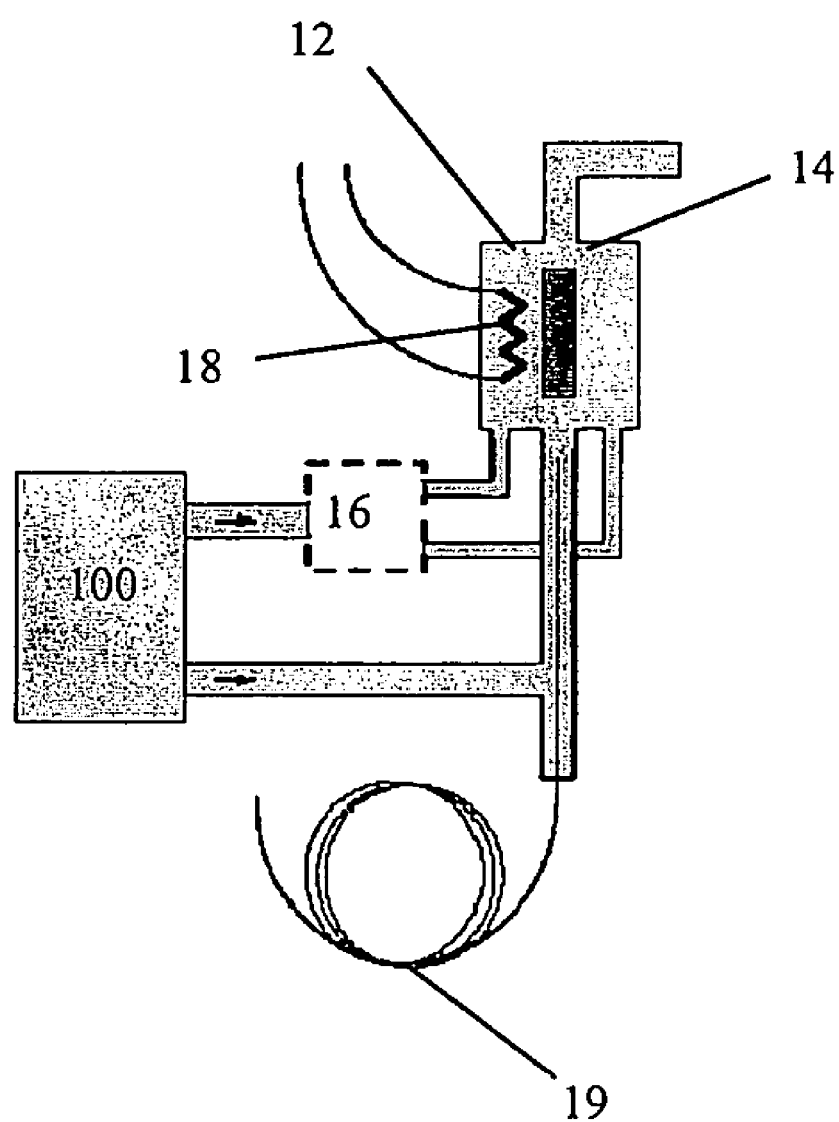
FIG. 1 is a depiction of a prior art single-filament TCD.
Figure 4A:
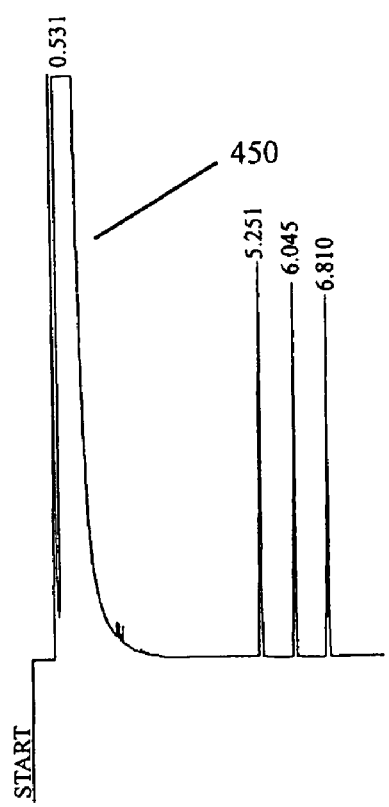
FIGS. 4A and 4B show, respectively, a chromatogram obtained using the prior art TCD illustrated in FIG. 1 and a chromatogram obtained using the TCD illustrated in FIGS. 2A and 2B that implements one embodiment of the present invention.
Figure 4B:
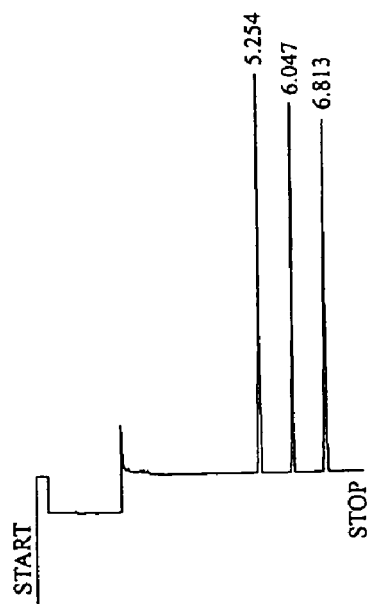

FIG. 4A illustrates a chromatogram of a sample obtained by the prior art single-filament TCD 10 illustrated in FIG. 1, while FIG. 4B illustrates a chromatogram of the same sample obtained by the single-filament TCD 20 illustrated in FIGS. 2A and 2B in accordance with one embodiment of the present invention. The sample is a standard mixture of 0.218 g/L n-Tetradecane, 0.218 g/L n-Pentadecane, 0.218 g/L n-Hexadecane in Hexane. The two experiments use the same gas chromatograph, the same column and the same operational parameters except the detectors. In the first experiment, TCD 10 is used and its switch valve 16 alternates at a frequency of 5 Hz throughout the whole experiment, giving rise to the chromatogram of FIG. 4A. In the second experiment, TCD 20 is used, and is set to work in "bypass" mode during the time period of 0.3 min–2.0 min and "normal" mode during the remaining time, giving rise to the chromatogram of FIG. 4B. In both experiments, Helium is used as the carrier gas. The flow of reference gas is 30 ml/min, while the flow makeup gas is 2 ml/min. The filament is maintained at 300° C.

The chromatogram of FIG. 4A contains a strong solvent-peak 450. In contrast, the strong solvent-peak 450 disappears in the chromatogram of FIG. 4B while the other peaks are not affected. The disappearance of the solvent-peak indicates that the solvent has circumvented the filament. The comparison between FIGS. 4A and 4B clearly shows that the mechanism employed in accordance with embodiments of the present invention permits an undesired compound to bypass the filament without adversely affecting the detection of the other compounds in the sample. Thus, the filament can be effectively protected from potential damage caused by the harmful compounds in the sample.

Although the present invention has been described above by way of examples, these examples are not intended to limit the scope of the present invention. Many modifications and variations are possible within the scope of the accompanying claims. It is to be understood that the spirit and scope of this invention is limited only by the terms of the following claims.

What is claimed is:

1. A process for protecting a filament in a thermal conductivity detector (TCD), comprising:
    switching a flow direction of column effluent in the TCD so that inert carrier gas and column effluent alternatively pass through the filament at a predetermined frequency;
    changing flow direction of column effluent in the TCD for a period of time other than the predetermined frequency to allow the column effluent to bypass the filament when an undesired compound appears in the column effluent; and
    changing the flow direction of the column effluent in the TCD to allow the column effluent to pass through the filament when the undesired compound disappears.

2. A process according to claim 1, wherein said TCD is a single-filament TCD comprising two cavities and said filament is suspended in one of the two cavities, and wherein said changing the flow direction of the column effluent in the TCD is achieved by switching a switch valve positioned before said filament.

3. A process according to claim 2, wherein a carrier gas flows through said switch valve, wherein the process further comprises causing said switch valve to alter the flow direction of the carrier gas by a controller such that the flow direction of the column effluent in the TCD is forced to change.

4. A process according to claim 1, further comprising: determining whether said undesired compound appears or not based on a Time Event Table, which records the estimated occurrence time period of said undesired compound.

5. A process according to claim 2, wherein said switching the switch valve is achieved by setting a flag stored in a controller of the TCD.

6. A thermal conductivity detector (TCD) for gas chromatograph, comprising:
    a first and a second cavity, each having a separate inlet and sharing a common inlet, said common inlet being coupled with the outlet of a chromatographic column;
    a switch valve coupled to a carrier gas supply source and the separate inlets of the first and second cavities;
    a filament positioned in the first cavity; and
    a controller coupled to said switch valve to control the switch valve to change the flow direction of the column effluent in the TCD (1) to allow the inert carrier gas and column effluent to alternatively pass through the filament at a predetermined frequency, (2) to allow the column effluent to bypass the filament for a period of time other than the predetermined frequency when an undesired compound appears in the column effluent and (3) to allow the column effluent to pass through the filament when the undesired compound disappears.

7. A TCD according to claim 6, wherein said controller includes a memory storing a Time Event Table, which records the estimated occurrence time period of said undesired compound.

8. A TCD according to claim 7, wherein said memory stores a flag, which corresponds to the status of said switch valve.

* * * * *